United States Patent [19]

Gabbay

[11] Patent Number: 4,741,328
[45] Date of Patent: May 3, 1988

[54] MEANS FOR INTRAAORTIC ASSIST AND METHOD OF POSITIONING A CATHETER THEREFOR

[76] Inventor: Shlomo Gabbay, 1 Randall Dr., Short Hills, N.J. 07078

[21] Appl. No.: 712,016

[22] Filed: Mar. 14, 1985

[51] Int. Cl.$^4$ .............................................. A61M 29/00
[52] U.S. Cl. ...................... 128/1 D; 604/99; 604/101; 128/673
[58] Field of Search .............. 128/1 D, 673, 692, 344; 604/96–101, 160

[56] References Cited

U.S. PATENT DOCUMENTS

| | | | |
|---|---|---|---|
| 3,533,403 | 10/1970 | Woodson | 128/419 P |
| 3,543,744 | 12/1970 | Lepar | 604/96 |
| 4,077,394 | 3/1978 | McCurdy | 128/1 D |
| 4,166,469 | 9/1979 | Littleford | 128/419 P |
| 4,284,073 | 8/1981 | Krause et al. | 128/1 D |
| 4,407,271 | 10/1983 | Schiff | 128/1 D |
| 4,473,067 | 9/1984 | Schiff | 128/1 D |
| 4,531,936 | 7/1985 | Gordon | 128/1 D |
| 4,540,404 | 9/1985 | Wolvek | 128/1 D |

*Primary Examiner*—William E. Kamm
*Attorney, Agent, or Firm*—Jordan B. Bierman

[57] ABSTRACT

A method and apparatus to provide an improved cardiac assist by the use of a new form of intraaortic balloon are described. A single small balloon may be placed in the ascending aorta close to the aortic valve, such a placement being effective to produce a substantially stronger augmentation of heart action than with the use of a longer balloon mormally placed, for example, in the descending aorta. Multiple small balloons positioned in the aortic arch, with or without a large balloon in the descending aorta, can be used to provide even stronger coronary flows. The external diameter of the balloons in their inflated condition should in all events never be so great as to block the aorta, even when the latter may become contracted. Further improvements include an external control portion adapted to permit redirection of the assist and simultaneous and continuous measurement of blood pressure. Slidable tubular members are employed to aid in the introduction of the cardiac assist into an appropriate artery and eliminate the need for wrapping the balloon around the assist prior to inserting it. This prevents complications in the use of the assist and avoids potential insertion malfunctions such as unwrapping.

26 Claims, 5 Drawing Sheets

MEANS FOR INTRAAORTIC ASSIST AND METHOD OF POSITIONING A CATHETER THEREFOR

The invention relates to an improved method and means for intraaortic heart assist, and generally to improved versions of the methods and means for such an assist disclosed in my copending application No. 430,039, filed 9/30/82, now U.S. Pat. No. 4,527,549. However, the improvements are applicable to other types of cardiac assists as well. More particularly, a novel arrangement for substantially increasing the cardiac output in patients suffering from heart failure is disclosed.

Counterpulsation by the placement of an inflatable balloon in the descending thoracic aorta, to provide diastolic augementation of blood pressure, has become a recognized procedure to aid cardiac output in certain conditions associated with myocardial failure, sometimes called Low Output Syndrome. A single inflatable balloon so positioned is inflated and deflated with a cycle appropriately timed to the normal heart beat. The inflatable balloon pump has become recognized as a useful, if imperfect, temporary tool whenever circulatory support is required.

The manner of synchronizing the action of the pump with the human heartbeat is well known in the art. In essence, a sensor is placed on an appropriate spot on the body which will permit the sensor to monitor the heartbeat. The pulse is converted into electrical impulses which are fed into a CPU which, in turn, controls the pump based thereon.

However, as discussed in U.S. Pat. No. 3,692,018, Goetz et al., issued Sept. 19, 1972, the simple balloon pump has its limitations. In order to provide a suitable pumping action, it has been made as large as possible with a cpacity of about 30 cc. The balloon's very position, in the descending aorta, results in a loss of pressure and pumping action about the heart where, for example, one desires to suffuse the coronary arteries. The shape of the large balloon prevents it from being pushed up about the aortic arch, closer to the heart.

The disadvantages and limitations of the prior art balloon pumps are overcome by the present invention, based upon the discovery supported by actual tests, that it is the position of the balloon pump, rather than its size, which plays an important role in its efficacy. More specifically, it has been found in acutal tests that a small balloon of about 10 cc capacity, if placed in the ascending aorta of a dog adjacent the aortic valve, can increase cardiac output by about 50 percent. This discovery is particularly fortuitous since it is possible to move a small balloon around the aortic arch into the ascending aorta. This was, of course, impossible with the larger size balloon heretofore thought to be necessary.

The invention does not mean that the use of a large balloon in the descending aorta is entirely discarded. As will be described hereinafter, the invention contemplates the use of a single small balloon adjacent the aortic valve either alone, in combination with a large balloon in the descending aorta, or with a series of additional small balloons serially connected between the first small balloon and the large balloon to substantially fill and create pressure and suction within the arch.

Accordingly, the principal object of the invention is to improve the heart assist procedure by the placement and development of a balloon pump and thereby increase cardiac output.

The aforesaid object is attained by positioning a balloon pump in the ascending aorta adjacent the aortic valve. The consequent further object of the invention is to provide a balloon pump structure which can be moved through the aortic arch to the desired position wihtout injuring the internal wall of the arch or the arteries branching therefrom.

A further object is to provide a heart assist procedure and device which will simplify the insertion and utilization of the device, by eliminating the need to wrap the balloons around itself and aid in simply and efficiently positioning the assist.

These and other objects and advantages of the present invention will become apparent from the following description thereof read in conjunction with the attached drawings.

DETAILED DESCRIPTION OF THE PREFERRED EMBODIMENT

Figure 1:
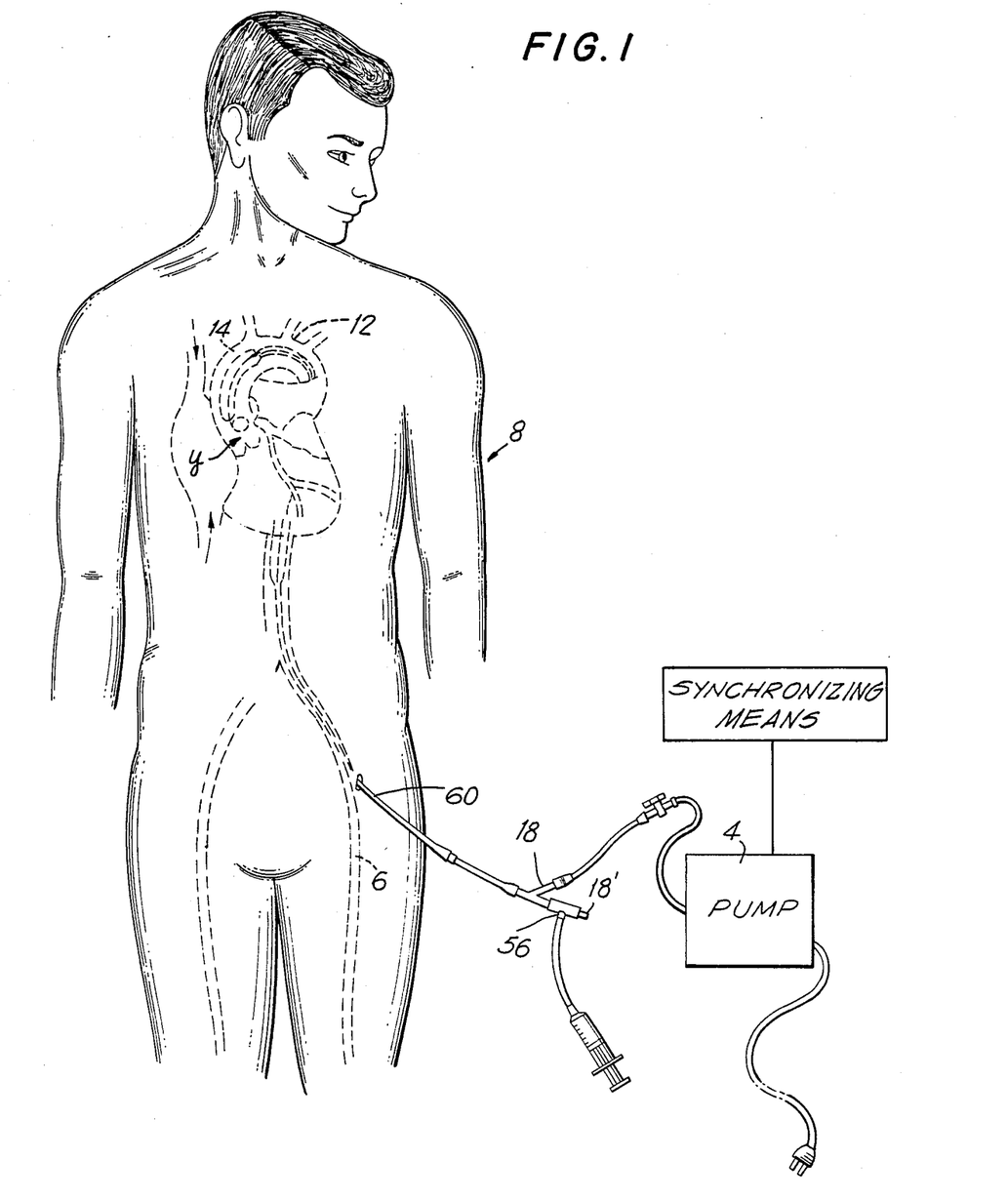
FIG. 1 is a fanciful view of portions of a human body broadly illustrating the invention and positioning of an intraaortic assist balloon pump.

FIG. 1 provides a setting for the invention illustrating procedures already known in the prior art modified according to the present invention. As there shown, an insertable portion 60 of a hollow catheter attached to pump 4 is inserted into an artery, preferably the femoral artery 6, within body 8. According to the present invention, the catheter is attached to a balloon or balloons (not shown) which are pushed from the femoral artery up through the descending aorta, about aortic arch 12 and into ascending aorta 14. The lead balloon, if there is more than one, comes to rest at point y immediately adjacent the aortic valve of heart 16. A wire (not shown) is fed into the catheter through connection 18' and extends through the catheter and all balloons, projecting from the front end of the lead balloon in a manner to be described later. A second connection 56 connects a pressure measuring device (not shown) to the hollow portions of the catheter, thereby allowing blood pressure within the aortic channel to be measured. The conenction to the pump is at 18.

More precise details of a preferred form of the invention are shown in FIGS. 2–12. As therein indicated, at one portion of catheter 2, an optional, but preferable, secondary balloon 20 is attached and positioned in descending aorta 10. A balloon of this relative size and in this position is known in the prior art and per se forms no part of the present invention except in association with the other balloon or balloons forming part of the invention. Beyond balloon 20 and extending through the aortic arch 12 and into the ascending aorta 14 are a series of optional small balloons 22. A first balloon 28, adjacent the aortic valve 30, is the most effective. At a minimum, balloon 28 is required.

All balloons, as is known in the art, will be made of a suitable inflatable, preferably nonthrombogenic material to avoid the danger of blood clotting; polyurethane is an example of such material. The balloons are interconnected with one another by small tubes 31 (FIG. 5) which, at least for interconnecting those balloons positioned in the aortic arch, may be formed with a slight arc to facilitate insertion and placement of the multiballoon structure. The ends of the balloons are appropriately bound or otherwise sealed to the outer surface of the tubes as indicated at 32. The space between catheter 2 and the balloons, together with the space between catheter 2 and tubes 31, comprise a balloon inflation/deflation pathway 46.

All of the balloons are designed to permit a limited radial expansion upon inflation so that in their inflated condition they do not block the aorta. It is known that the aorta is distensible and if the patient is in shock with low blood pressure, the diameter of the aorta may contract. If so, and the diameter of the inflated balloon is not limited, it may effectively block the aorta. This has been found not only to reduce the effectiveness of the cardiac assist, but, in the extreme case with full blocking, can result in a reverse pumping action. Accordingly, limiting the diameter of the intraaortic assist balloon is an important feature of my invention.

As previously indicated with reference to FIG. 1, extending from connection 18' and through catheter 2 and the balloons is wire 34 which protrudes from a first insertion end of catheter 2. The open end of catheter 2 is not totally blocked by wire 34; the hollow regions of catheter 2 are sensitive to blood pressure, and this pressure can be measured by connecting the other end of catheter 2 to a known type of instrument. That portion of the hollow wire in the balloons to be positioned in the aortic arch may be formed wiht a slight curve or arc to facilitate placement and insertion of the multiballoon structure; such an arrangement would be used with arcuate connecting tubes, as described above.

Figures 3, 4, 5, 6:
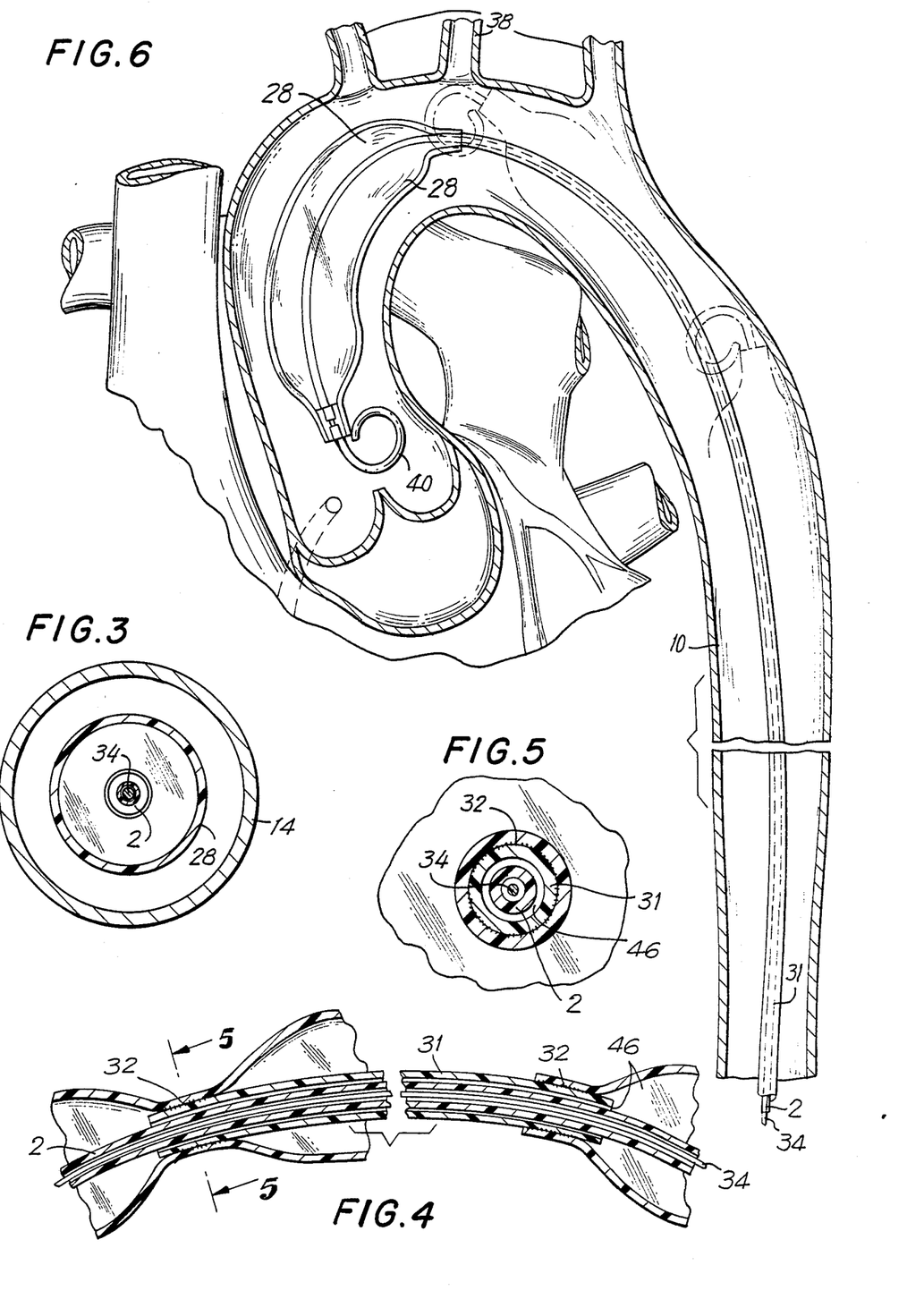
FIG. 3 is a cross-sectional view through the ascending aorta and the implanted balloon pump, taken along the line 3—3 of FIG. 2.
FIG. 4 is a cross-sectional view along the line 4—4 of FIG. 2 illustrating details of interconnected balloons forming the pump.
FIG. 5 is a transverse cross-sectional view along the line 5—5 of FIG. 4.
FIG. 6 is a view similar in part to FIG. 2, shown in cross-section, of a modified form of balloon pump.

FIG. 6 illustrates variations in the present invention involving significantly useful features. As previously indicated, movement of balloon 28 should proceed about aortic arch 12 in such a manner as to avoid damage to both the inner wall of the arch and the openings to carotid arteries 38. To assist in easing the balloon about the arch, insertion end 36 (see FIG. 8) may be formed with tubular tip 40, preferably curved in such a way that it will ride against the inner wall of the arch, as shown in dotted lines.

Balloon 28 should be mounted with respect to catheter 2 such that the is larger than tubes 31, thus creating a larger soft outer cushion contacting the inner surface of the arch as it is pushed around, thereby aiding the cardiac assist in traversing the aortic arch.

Other variations in the invention, but falling within the scope thereof, will occur to those skilled in this art. The actual number and size of the balloons in the form of invention shown in FIG. 2 may be varied within the limits that such balloons must be capable of smooth movement about the inner wall of the aortic arch. The manner of interconnecting the balloons is not critical as long as there is a proper seal between adjacent balloons and provision is made for catheter 2, wire 34 and inflation/deflation pathway 46.

The intraaortic caridac assist preferably has a control portion 42 (shown in FIG. 8) which comprises a housing containing a non-insertable end of catheter 2. First access 18, connecting inflation/deflation pathway 46 with means 4 for inflating and deflating the balloons, is provided and sealed off from the remainder of the housing interior by first seal 50. Wire 34 emerges through the non-inserted open end of catheter 2 and passes through second seal 52 to terminate in control tip 54. Second seal 52 is preferably capable of forming a seal around wire 34 while permitting movement of the wire, including the wire's withdrawal from the assist, without compromising the seal. It is therefore preferable to use a resilient foam material for second seal 52. Control tip 54 is capable of rotating wire 34 about its longitudinal axis.

Housing 44 also comprises second connection 56, in operative relation with the hollow interior portions of catheter 2. Second connection 56 is connected, when desired, to a device for measuring blood pressure, not shown.

Figures 9, 10:
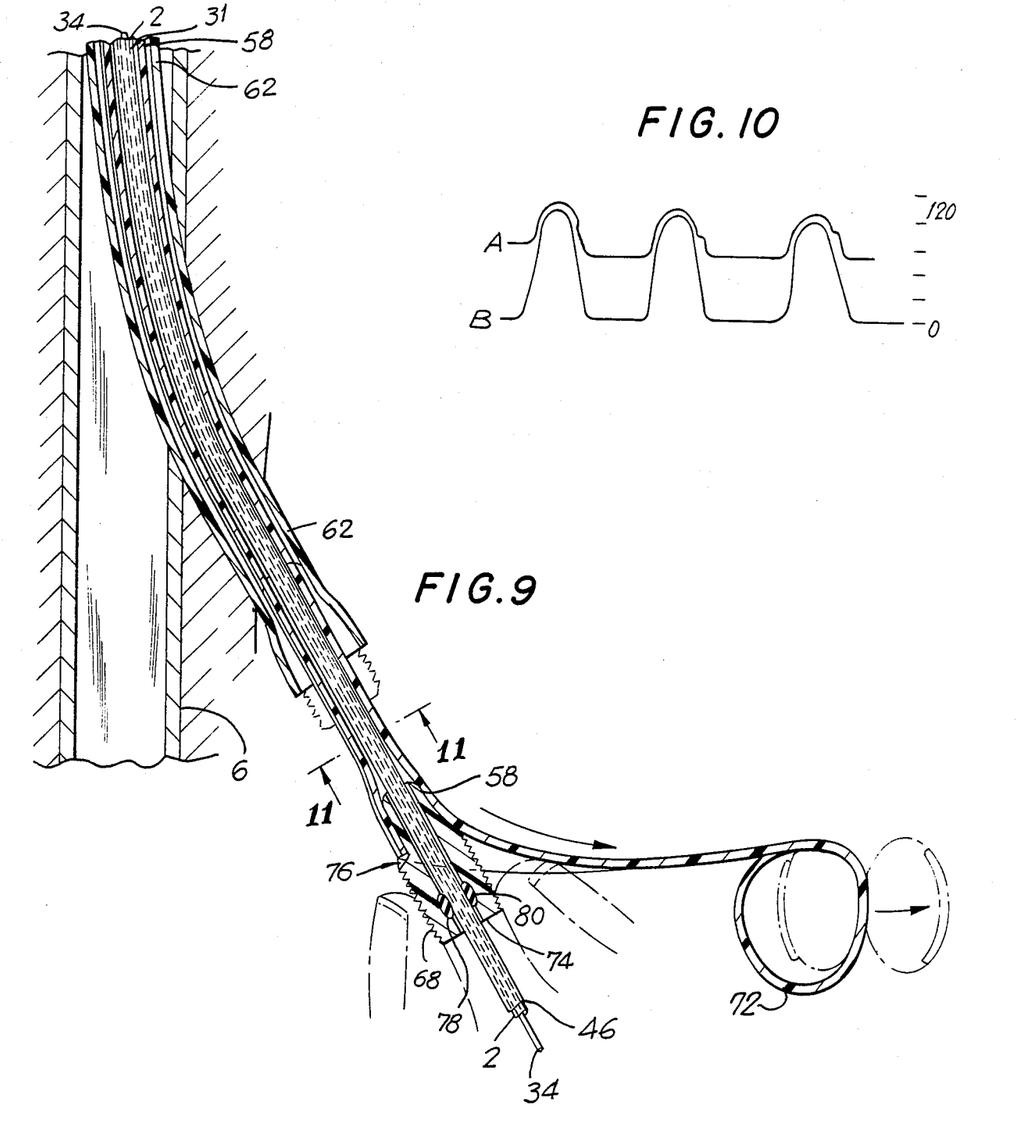
FIG. 9 is an enlarged view of the non-inserted portion of the assist during removal of the first slidable member.
FIG. 10 is a graph of representive pressure curves as measured in the aorta and vertricle respectively.
Figure 11:
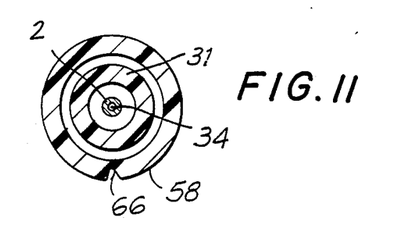
FIG. 11 is a cross sectional view of FIG. 9 along line 11—11.
Figure 12:
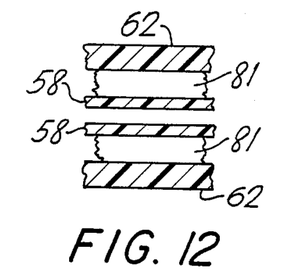
FIG. 12 is a fragmented cross-sectional view showing an inflatable sphincter.

Furthermore, the cardiac assist pump of the invention preferably has two tubular slidable members in association therewith as shown in FIG. 9. First hollow slidable member 58 is positioned about the insertable portion. It is of sufficient length to contain therein segment 64 (see FIG. 8) comprising tubular tip 40, which, if curved, has been straightened, first balloon 28, and any secondary balloons present, and all regions therebetween. The inside diameter of first slidable member 58 is as small as practicable yet large enough to allow passage of the cardiac assist pump therethrough. The assist is inserted into slidable member 58 with the aid of a medical lubricant.

A portion of second slidable member 62 is inserted in artery 6. Slidable member 62 is of such diameter as to be capable of accepting therein and allowing passage therethrough of slidable member 58 and segment 64.

It is advantageous to provide at least one longitudinal slot 66 in first slidable member 58 and a slicing member 68, which is preferably around the outside of the inflation/deflation pathway 46 and capable of being urged against first slidable member 58. Slidable member 58 is urged against slicing member 68 as member 58 is withdrawn from the body and out of second slidable member 62. It is most preferable that slicing member 68 have a cutting edge 76 which may be directed into slot 66.

Preferably, all of first slidable member 58 is removed; however, a retained portion which would otherwise be the last portion of member 58 to be removed from the body, may be broken away and used to help form a seal between the caridac assist proper (without the slidable members), and the second slidable member 62. It is also helpful for the first slidable member 58 to have, as a portion thereof, a pull ring 72 for withdrawing member 58 from the body and member 62; although any means of gripping first slidable member 58 for removal thereof will suffice.

To further seal off and prevent undesirable blood flow out of the artery in which the cardiac assist has been inserted, slicing member 68 and cutting edge 76 are made to be portions of third sealing means 74. This sealing means is preferably made of resilient material and is capable of having a portion thereof urged, by manual pressure, into first slidable member 58. Upon removal of member 58, third sealing means 74 is either urged into second slidable member 62 or, if already therein, is capable of expanding to fill second slidable member 62 and thereby seal the the area between the cardiac assist (without member 62) and member 62.

Third sealing member 74 should have sufficient resilience to resist movement thereof due to the action of blood pressure thereon. However, its resistance to movement should be sufficiently small that ordinary manual pressure is capable of moving the sealing member as desired. As a further aid to providing such a sealing member, an indentation 78 may be provided on the surface of sealing member 74, which surface is in contact with the outer surface of the assist (absent the slidable members). In conjunction therewith, a small ring 80 may be provided at an appropriate distance to act as a catch for the third sealing means.

As an alternative to the third sealing means, second slidable member 62 may have an inflatable sphincter 81 (see FIG. 12) along the internal walls thereof so that, upon inflation of the sphincter, no appreciable blood flow results. These alternatives may be used separatedly or in conjunction with one another.

The overall procedure for providing maximum cardiac assist utilizing the multiballoon pump of FIGS. 2-11 will now be described. The series of interconnected balloons, in the deflated state, with wire 34 and cathter 2 attached, is introduced into an artery, preferably femoral artery 6, and slowly urged up the descending aorta 10 and into the aortic arch 12. Preferably, prior to movement of the small balloons into the aortic arch, the balloons are inflated and since balloons 28 and 22 are small and of limited diameter, as previously discussed, they easily conform to the shape of the aortic arch and ride along its inner surface without abrading the same. Likewise, the small ballons do not catch and perhaps injure the openings to carotid arteries 38.

Tests have indicated that the significance of the balloon pump according to the present invention lies in the placement of a balloon in the ascending aorta adjacent aortic valve 30. In order to properly position first balloon 28, the inflated balloon series is urged upwardly until balloon 28 moves around the arch and downward a sufficient distance into the ascending aorta to open aortic valve 30. This point, when the tip is in the ventricle, will immediately show a drop in the diastolic pressure curve, (the ventricular systolic pressure is the same as in the aorta but the diastolic pressure will drop to zero instead of the normally observed aortic diastolic pressure) as monitored through catheter 2 and second connection 56. The balloon is then slowly withdrawn, perhaps one-half inch, until aortic valve 30 closes, as indicated when the measured blood pressure shows the typical aortic pressure curve, both at systole and diastole. (These curves are illustrated in FIG. 10. The typical aortic curve is shown as A, while the ventricular pressure curve is B). This is the point of optimum positioning of the forward balloon 28. Counterpulsation by pump 4 may then be started in synchronism with the normal heart beat in a manner well known in the art.

The ability to continuously monitor blood pressure while directing the insertion end of the assist pump is extremely important. In directing the first balloon to a position adjacent the aortic valve, the valve is forced open. Intermittent monitoring of blood pressure results in guessing how far to insert the device, with potential injury to the heart. In addition, the redirecting ability of the wire allows the device to more easily traverse the aortic arch. Therefore, the combination of these features provides a safer, more reliable cardiac assist.

The improved cardiac assist described above is also easier to insert into an artery than prior known devices. In FIG. 9, slidable member 58, having segment 64 therein, is inserted into slidable member 62, already partially inserted into the selected artery, and passes therethrough. Slidable member 58 is preferably at least 3" longer than slidable member 62. Upon member 58 emerging from member 62 within artery 6, the cardiac assist is further inserted, thereby forcing insertable portion 60 (see FIG. 1) to emerge from member 58 into artery 6.

Member 58 can be advantageously removed and torn away from the device, using slicing member 68, once the inserted end thereof has emerged from second slidable member 62 into the artery. Other points of removal of member 58 may be used and will be apparent to those skilled in the art. The device may also be utilized without ever removing member 58, if so desired. The assist is then moved further into the aorta in the usual manner to be positioned as set forth above.

The assist may be constructed so that the first slidable member has therein, at the end thereof which is not inserted into the body, a portion of third sealing means 74. Such a construciton will effectively halt bleeding around the assist during its stay within the body. Sealing means 74 is preferably tapered so that its wider portion is larger in diameter than second slidable member 62. The slidable memberless assist is inserted, along with first slidable member 58, into second slidable member 62. Upon reaching the end of first slidable member 58, or the maximum insertion, whichever is first, pull ring 72 is pulled back, forcing slot 66 against cutting edge 76. First slidable member 58 is pulled further until all but a minor portion thereof is removed or it is entirely removed. When third sealing means 74 is not utilized, any member providing a sharp edge with which to cut or break first slidable member 58 may be used. A further refinement is that the third sealing means 74 is capable of locking onto first slidable member 58 and/or second slidable member 62.

When a sphincter is employed in place of the third sealing means, it is inflated to prevent blood flow from second slidable member 62. Upon inserting the first slidable member with the assist therein, the sphincter is deflated to allow first slidable member 58 to pass therethrough. Once the edge of first slidable member 58 has been inserted beyond sphincter 82, the sphincter is reinflated to reseal the area.

Once sealing means 74 is in place against second slidable member 62, further adjustments in the placement and operation of the assist can be accomplished without undesired bleeding at the insertion site.

The insertion as described above provides a maximum cardiac support. At the time of systole, blood is practically sucked from the heart, so that at the time of diastole coronary perfusion is increased 50-300%. This is of particular significance with reference to the adjacent coronary arteries 38. On the other hand, as previously discussed, a significant feature of the present invention lies in the discovery that a single small balloon, if properly placed, may provide a significant improvement in cardiac assist even without the use of the formerly used large balloon in the descending aorta and/or the intermediate small balloons shown in FIG. 2. A significant improvement will be obtained with a single small balloon 28 alone, as shown in FIG. 6, supplemented in some cases with just the large balloon 20 connected to balloon 28 by inflation/deflation pathway 46.

Figure 2:
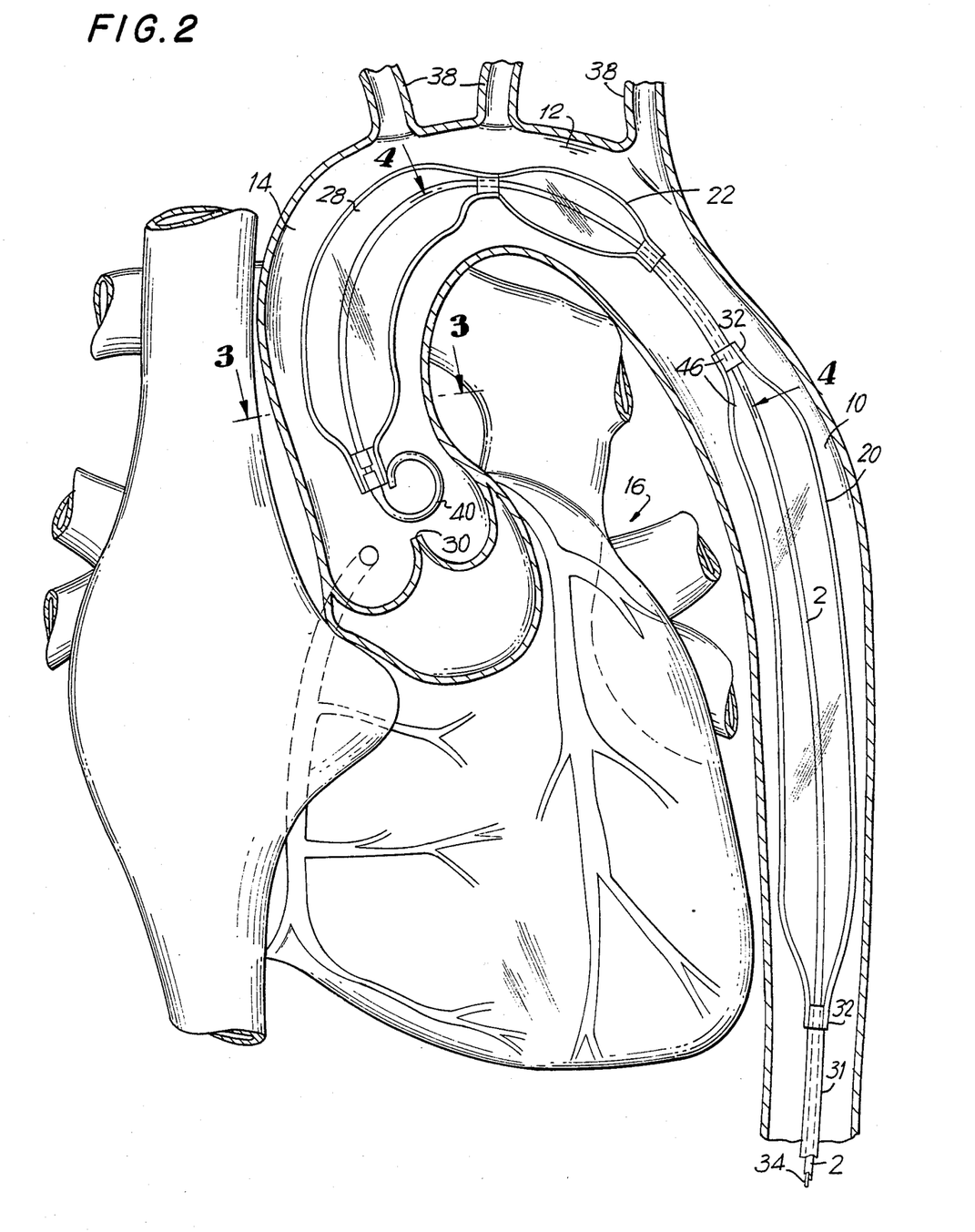
FIG. 2 illustrates the human heart and associated arteries showing, in cross-section, the positioning of a balloon pump according to this invention within the descending aorta, the aortic arch and the ascending aorta.
Figures 7, 8:
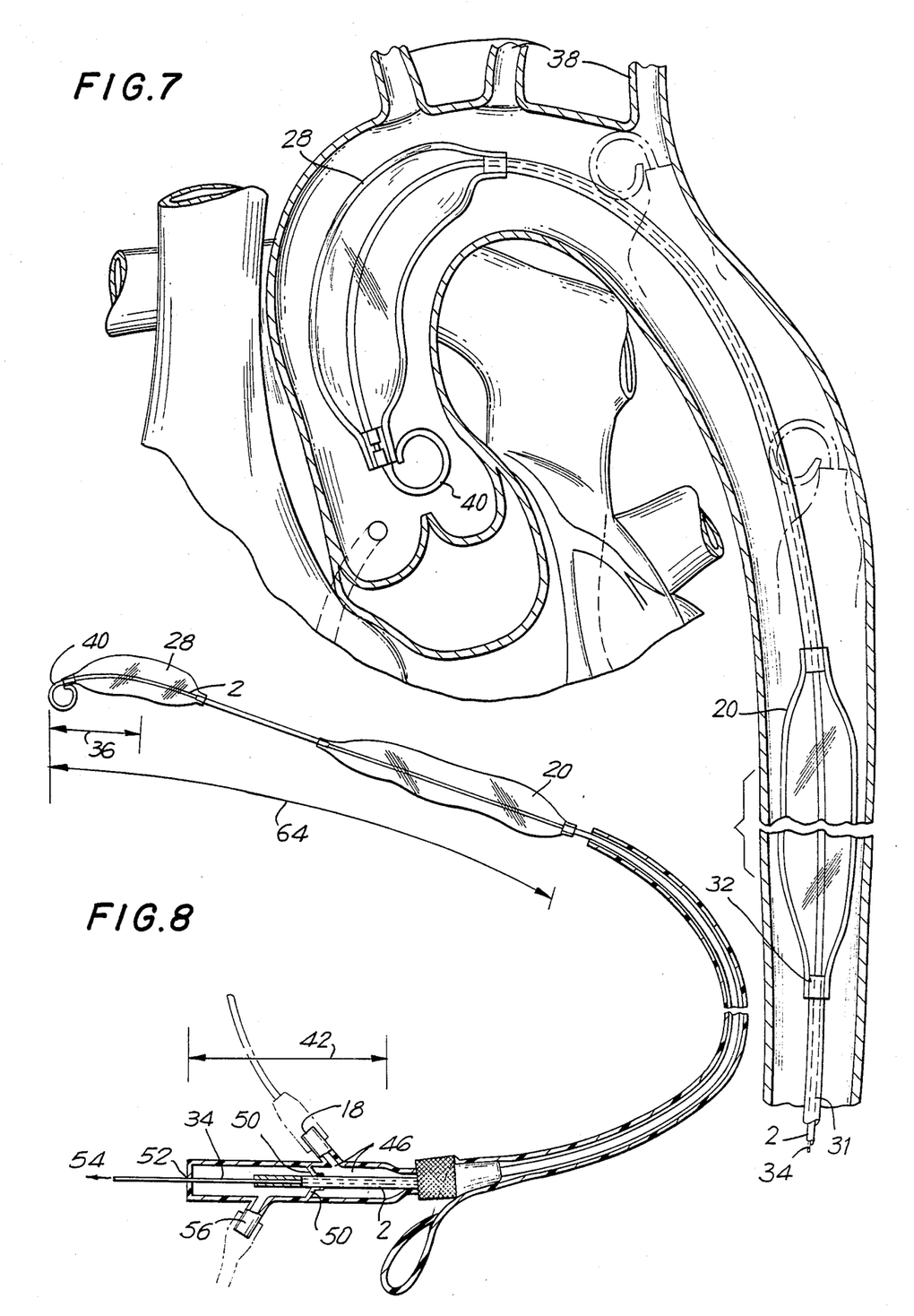
FIG. 7 is a view similar to FIG. 6, showing a still further modified form of balloon pump.
FIG. 8 shows one embodiment of the invention prior to insertion into a body.

Attention is directed to the fact that, as shown in FIGS. 2 and 7, balloon 28, positioned in the ascending aorta, may be of substantially greater diameter than the balloons positioned in either the aortic arch or the descending aorta. This arrangement, which adds to the effectiveness of balloon 28, is made possible by the fact that the ascending aorta, as shown, is generally of greater diameter than the descending aorta. Thus the use of larger balloons in the critical position next to the aortic valve and the coronary arteries is made possible by taking advantage of the natural difference in size of the two aortic regions.

The invention as above described fulfills the objectives previously stated, both as a novel medical procedure and novel apparatus for carrying out such procedure. Depending upon the effect desired, a one, two or multiple balloon system is available. The large balloon may be omitted whether one or a plurality of small balloons are used. Total balloon capacity can vary from 10 cc for one balloon as in FIG. 6 to 60 cc with a full balloon system as in FIG. 2 depending upon the amount of cardiac assist required.

As previously emphasized, however, placement of the forward balloon is of special significance and increases the amount of caridac assist by a ratio far in excess of the mere sum of balloon capacity.

The invention is accordingly not to be considered as restricted to the exact embodiments shown and described, but only as may be limited by the claims which follow.

I claim:

1. An intraaortic cardiac assist balloon pump having a first portion and a second portion, said first portion comprising
   (a) a catheter having a first end and a hollow portion terminating adjacent said first end, said first end being insertable into an artery,
   (b) a first inflatable balloon and an inflation/deflation pathway in connection with said first balloon, both said first balloon and said pathway surrounding at least a part of said catheter,
   (c) means, connected to said pathway at a first access which is remote from said first balloon, for inflating and deflating said first balloon in synchronism with a heartbeat, and
   (d) sensor for operative connection with a blood pressure measuring device, said sensor operative connection to said sensor, said sensor extending to a point adjacent said first end,
said second portion at least partly outside said artery and including a control portion comprising a redirecting means and a control tip remote from said first end, said redirecting means extending from said control tip to a point adjacent said first end, whereby manipulation of said control tip causes reorientation of said catheter.

2. The pump of claim 1 wherein said sensor is adjacent said hollow portion.

3. The pump of claim 2 wherein there is a tubular tip connecting the environment adjacent said tubular tip with said hollow portion.

4. The pump of claim 1 wherein said redirecting means comprises a wire in said hollow portion, said hollow portion being of greater cross-section than said wire, whereby manipulation and blood pressure measuring can be carried out simultaneously.

5. The pump of claim 1 wherein said control means is provided with a housing adjacent said control tip, said control tip passing through said housing and extending therebeyond.

6. The pump of claim 1 further comprising a sealing means isolating said first access and said pathway from said hollow portion.

7. The pump of claim 6 wherein said sealing means comprises said second tubular member having an inflatable sphincter along the internal circumference thereof for contacting, upon inflation, said first slidable tubular member or said catheter and effectively inhibits undesirable blood flow from internal portions of said second slidable member.

8. The pump of claim 1 wherein said first balloon is arcuate in shape.

9. The pump of claim 1 wherein said first balloon is non-occlusive of the aorta when in place and inflated.

10. The pump of claim 1 comprising at least one secondary non-occlusive balloon on said first portion at a distance from said first balloon such that, upon positioning said first balloon adjacent an aortic valve, said second balloon is in an aortic arch or a descending aorta and is operatively connected to said pathway.

11. The pump of claim 10 wherein said distance is such that said second balloon is in said aortic arch when said first balloon is in an ascending aorta.

12. An intraaortic cardiac assist balloon pump having a first portion and a second portion, said first portion comprising
   (a) a catheter having a first end insertable into an artery,
   (b) a first inflatable balloon and an inflation/deflation pathway in connection with said first balloon, both said first balloon and said pathway surrounding at least a part of said catheter,
   (c) means, connected to said pathway at a first access which is remote from said first balloon, for inflating and deflating said first balloon in synchronism with a heartbeat, and
   (d) sensor for operative connection with a blood pressure measuring device, said sensor operative connection to said sensor, said sensor extending to a point adjacent said first end,
said second portion connected to said catheter at a point remote from said first end and being at least partly outside said artery, a first slidable tubular member loosely surrounding a segment of said first portion, said segment including a tubular tip, said first balloon, and the parts of said first portion therebetween, said tubular tip attached to said catheter adjacent said first end and being curved.

13. The pump of claim 12 comprising at least one secondary non-occlusive balloon on said first portion at a distance from said first balloon such that, upon positioning said first balloon adjacent an aortic valve, said secondary balloon is in an aortic arch or a descending aorta and is operatively connected to said pathway.

14. The pump of claim 13 wherein said segment contained within said slidable tubular member further comprises said secondary balloon and all portions of said first portion between said first balloon and said secondary balloon.

15. The pump of claim 12 further comprising a second slidable tubular member for receiving said first slidable tubular member whereby, when said second slidable member is at least partially introduced into an artery, said first slidable member containing said segment may be passed through said second slidable member to introduce said first end into said blood vessel.

16. The pump of claim 15 wherein said first slidable tubular member has a ring portion on an end which is not inserted to allow withdrawal of said first slidable tubular member and a longitudinal slot therein whereby said first slidable tubular member can be cut or broken as said first slidable member is withdrawn from said second slidable member.

17. The pump of claim 12 further comprising a sealing means on and around the outer periphery of said first portion which sealingly contacts said first portion and either said first slidable tubular member or said second slidable tubular member.

18. The pump of claim 17 wherein said sealing means has thereon an edge adapted to contact said first slidable tubular member and thereby to be capable of cutting or breaking said first slidable tubular member upon withdrawal of said first slidable tubular member from said second slidable tubular member.

19. The pump of claim 12 wherein said second slidable tubular member further comprises an inflatable sphincter along the internal circumference thereof for sealably contacting, upon inflation, said first slidable member or said catheter and effectively inhibits undesirable blood flow from internal portions of said second slidable member.

20. A method of positioning a catheter in an aorta comprising inserting a first end of said catheter into said aorta, monitoring a normal blood pressure in said aorta and adjacent said first end at least while said first end is adjacent an aortic valve, noting a drop in diastolic pressure when said first end passes said aortic valve, and withdrawing said first end to a position adjacent said aortic valve.

21. The method of claim 20 further comprising sliding a first tubular slidable member onto said catheter to encompass a first inflatable balloon, said first end, and the parts of said catheter therebetween before insertion of said catheter into an artery.

22. The method of claim 21 comprising withdrawing said first slidable member after insertion of said catheter and said first slidable member into said aorta, thereby exposing said balloon.

23. The method of claim 20 further comprising withdrawing and breaking or cutting a first slidable tubular member which loosely surrounds a segment of a first insertable portion of said catheter.

24. The method of claim 20 comprising withdrawing said first end until said diastolic pressure returns to said normal blood pressure.

25. The method of claim 20 further comprising noting said blood pressure continuously once begun at least until said cardiac assist is properly in place.

26. The method of claim 20 wherein said catheter comprises a first inflatable balloon and an inflation/deflation pathway in connection with said first balloon, both said first balloon and said pathway surrounding at least a part of said catheter, said first balloon being stored outside of a sleeve surrounding said catheter, said method further comprising withdrawing said balloon into said sleeve before inserting said first end into said artery, inserting said first end into said artery, and then withdrawing said sleeve, thereby exposing said balloon.

* * * * *